(12) United States Patent
Spiegel et al.

(10) Patent No.: US 12,721,922 B2
(45) Date of Patent: Sep. 1, 2026

(54) DIFFUSER HAVING MULTIPLE ATOMIZERS WITH A SINGLE PUMP

(71) Applicant: Ideal Living, LLC, Sherman Oaks, CA (US)

(72) Inventors: Peter G. Spiegel, Sherman Oaks, CA (US); Michael Pedersen, Sherman Oaks, CA (US)

(73) Assignee: Ideal Living, LLC, Sherman Oaks, CA (US)

( * ) Notice: Subject to any disclaimer, the term of this patent is extended or adjusted under 35 U.S.C. 154(b) by 621 days.

(21) Appl. No.: 17/939,558

(22) Filed: Sep. 7, 2022

(65) Prior Publication Data

US 2023/0080109 A1 Mar. 16, 2023

Related U.S. Application Data

(60) Provisional application No. 63/353,423, filed on Jun. 17, 2022, provisional application No. 63/244,526, filed on Sep. 15, 2021.

(51) Int. Cl.
*A61L 9/14* (2006.01)

(52) U.S. Cl.
CPC ............. *A61L 9/14* (2013.01); *A61L 2209/11* (2013.01); *A61L 2209/134* (2013.01)

(58) Field of Classification Search
CPC . B05B 17/0646; B05B 17/0684; B05B 12/08; B05B 11/1084; B05B 11/0078; A61L 9/14; A61L 2209/133; A61L 2209/111; A61L 9/125; A61L 9/035
See application file for complete search history.

(56) References Cited

U.S. PATENT DOCUMENTS

2015/0297779 A1* 10/2015 Conroy ..................... A61L 2/00 239/74
2019/0118210 A1 4/2019 Freeman
2020/0215219 A1 7/2020 Becker
2020/0251210 A1 8/2020 Skoda
2020/0289694 A1* 9/2020 Kelsen .................... A61L 9/122

FOREIGN PATENT DOCUMENTS

CN 205964560 U 2/2017
FR 2911783 A1 8/2008
JP 2019126538 A 8/2019
KR 1020190037052 A 4/2019

OTHER PUBLICATIONS

"Aromaestro Cartridges for Precise, High Performance Nebulization", Aromaestro, 2020, pp. 1-5.
International Search Report & Written Opinion for PCT Application No. PCT/US2022/042745 mailed Dec. 27, 2022 (12 pages).

* cited by examiner

*Primary Examiner* — Christopher R Dandridge
(74) *Attorney, Agent, or Firm* — Eversheds Sutherland (US) LLP

(57) ABSTRACT

A diffuser having a plurality of atomizers associated with a single pump is provided. The diffuser may include four or more atomizers that may be removably coupled to the diffuser. Each atomizer may store the same or different oils. In some embodiments, the outlet of the atomizer may have a tortuous passageway to prevent diffusion of large oil droplets. The diffuser includes a plurality of valves associated with the plurality of atomizers, such that the valves may be selectively actuated to permit flow to the selected atomizers.

20 Claims, 10 Drawing Sheets

DIFFUSER HAVING MULTIPLE ATOMIZERS WITH A SINGLE PUMP

CROSS-REFERENCE TO RELATED APPLICATIONS

This application claims priority to U.S. Provisional Patent Application No. 63/244,526 filed Sep. 15, 2021, and U.S. Provisional Application No. 63/353,423 filed Jun. 17, 2022, which are both hereby incorporated by reference herein in their entireties.

BACKGROUND

Current diffusers include a single atomizer associated with a single pump for diffusing oils. Moreover, large oil droplets may be diffused through the atomizer, which may cause staining of surrounding surfaces upon diffusion.

It is with respect to these and other considerations that the disclosure made herein is presented.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Figure 1B:
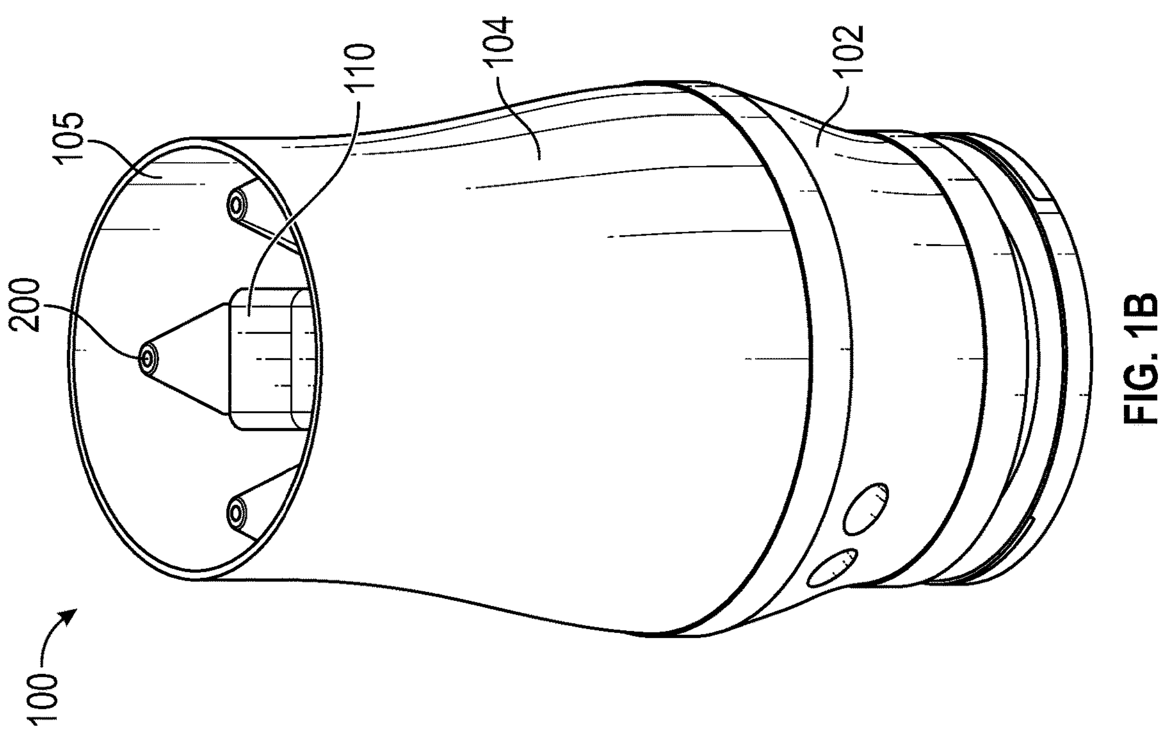
FIG. 1B depicts a perspective view of the diffuser of FIG. 1A

This disclosure generally relates to diffusers, atomizers, and the components thereof. In some instances, a diffuser is provided. The diffuser may include a pump and a plurality of atomizers. Each atomizer of the plurality of atomizers may be coupled to the pump via a respective conduit. Each of the respective conduits may be associated with a valve. The valve may selectively permit flow from the pump to each of the plurality of atomizers.

In other instances, an atomizer is provided. The atomizer may include a connection portion that may be removably and fluidicly coupled to a chamber portion, which may contain oil. The connection portion may have an inlet, an outlet, and a discharge chamber. The inlet may be coupled to a pump. The outlet may include a tortuous pathway. The tortious pathway may prevent diffusion of droplets of the oil from exceeding a predetermined size upon actuation of the pump. The discharge chamber may be in fluid communication with the inlet and the outlet.

In further instances, a diffuser having an oil balancer is provided. The diffuser may include a pump and a plurality of atomizers. Each atomizer of the plurality of atomizers may be coupled to the pump via a respective conduit. Each of the respective conduits may be associated with a valve. The valve may selectively permit flow from the pump to each of the plurality of atomizers. The oil balancer may include a plurality of RFID readers, a plurality of RFID tags, and a controller. The oil balancer may be effective to control the rate of flow from the pump to the respective atomizer, as to enable balanced simultaneous diffusion.

The disclosure will be described more fully hereinafter with reference to the accompanying drawings, in which example embodiments of the disclosure are shown. This disclosure may, however, be embodied in many different forms and should not be construed as limited to the example embodiments set forth herein. It will be apparent to persons skilled in the relevant art that various changes in form and detail can be made to various embodiments without departing from the spirit and scope of the present disclosure. Thus, the breadth and scope of the present disclosure should not be limited by any of the above-described example embodiments but should be defined only in accordance with the following claims and their equivalents. The description below has been presented for the purposes of illustration and is not intended to be exhaustive or to be limited to the precise form disclosed. It should be understood that alternate implementations may be used in any combination to form additional hybrid implementations of the present disclosure. For example, any of the functionality described with respect to a particular device/component may be performed by another device/component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments.

Certain words and phrases are used herein solely for convenience and such words and terms should be interpreted as referring to various objects and actions that are generally understood in various forms and equivalencies by persons of ordinary skill in the art.

Figure 1A:
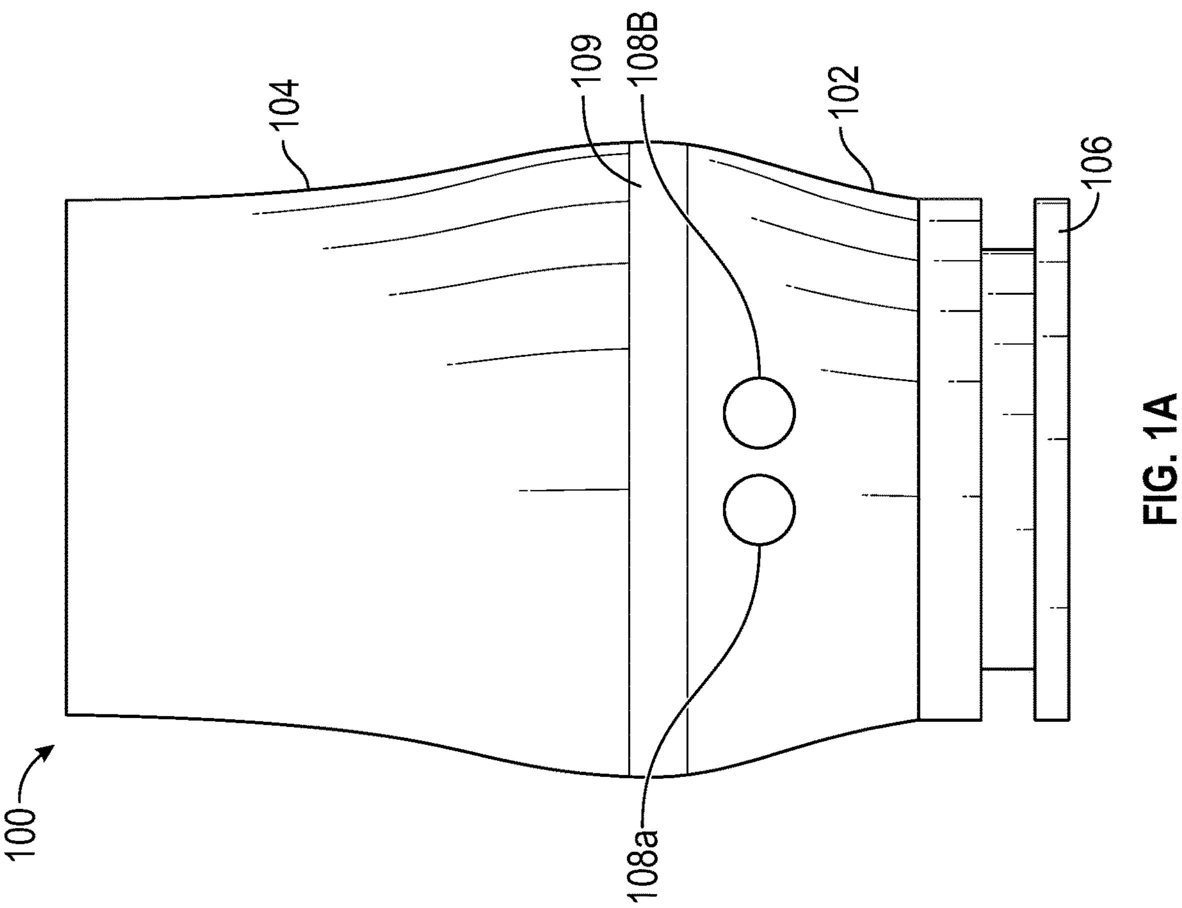
FIG. 1A depicts a front view of a diffuser, in accordance with one or more embodiments of the disclosure.

Referring now to FIGS. 1A and 1B, an exemplary diffuser is provided. Diffuser 100 may include base portion 102 and cover 104, which may be removably coupled to base portion 102. Base portion 102 and cover 104 may have a circular shape, and when coupled together, the diameter of diffuser 100 may increase from the bottom surface of base portion 102 toward the top surface of base portion 102, and decrease from the bottom edge of cover 104 toward the top edge of cover 104. As shown in FIG. 1A, base portion 102 may include one or more actuators, e.g., actuators 108*a*, 108*b*, which may be actuated by a user to execute a function of diffuser 100. For example, actuator 108*a* may be actuated by a user to turn diffuser 100 on/off, and actuator 108*b* may be actuated by a user to activate light 109 of diffuser 100. In addition, base portion 102 may include one or more legs 106 for positioning and stabilizing diffuser 100 upright.

As shown in FIG. 1B, diffuser 100 further may include stem portion 110 extending vertically from base portion 102, such that cover 104 covers stem portion 110 when cover 104 is coupled to base portion 102. As described in further detail below, stem portion 110 may be removably coupled to plurality of atomizers 200 for diffusing one or more scented oils. As shown in FIG. 1B, cover 104 may include opening 105, such that diffused oils vapor may exit the plurality of atomizers 200 into the surrounding air.

Figure 2B:
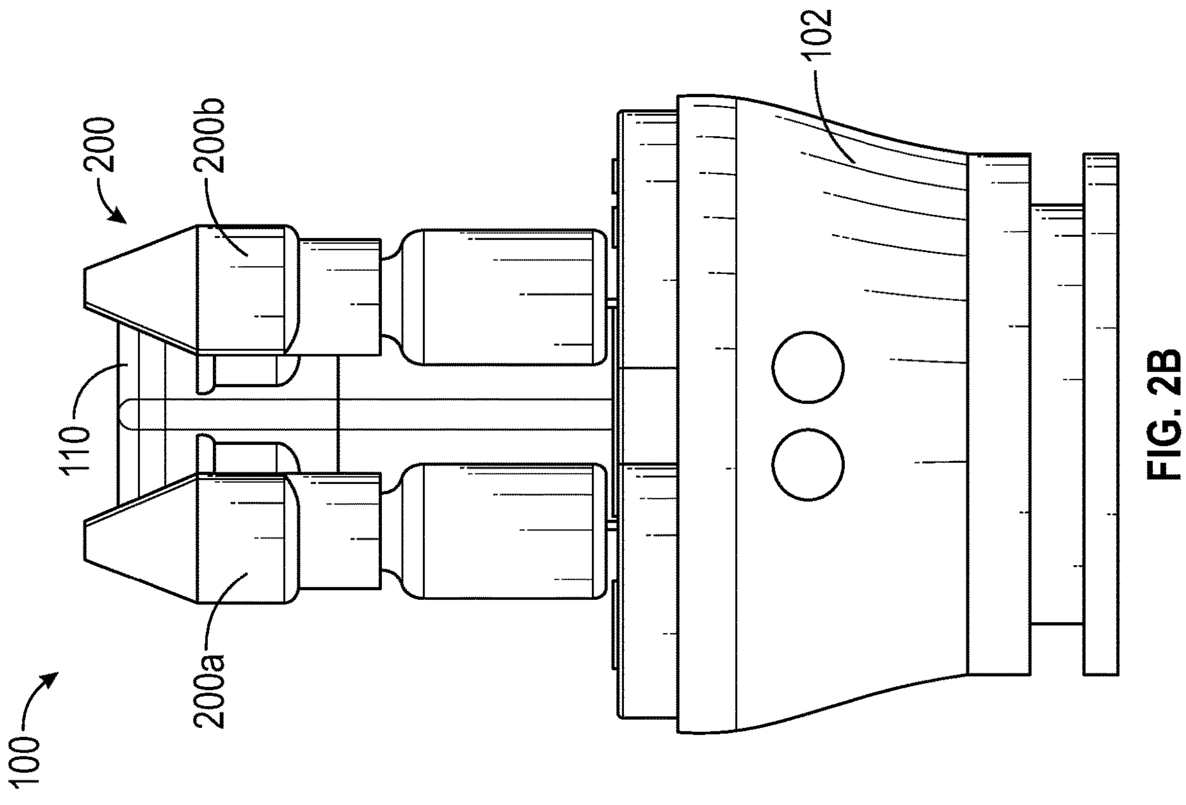
FIG. 2B depicts a front view of the diffuser of FIG. 2A.
Figure 2A:
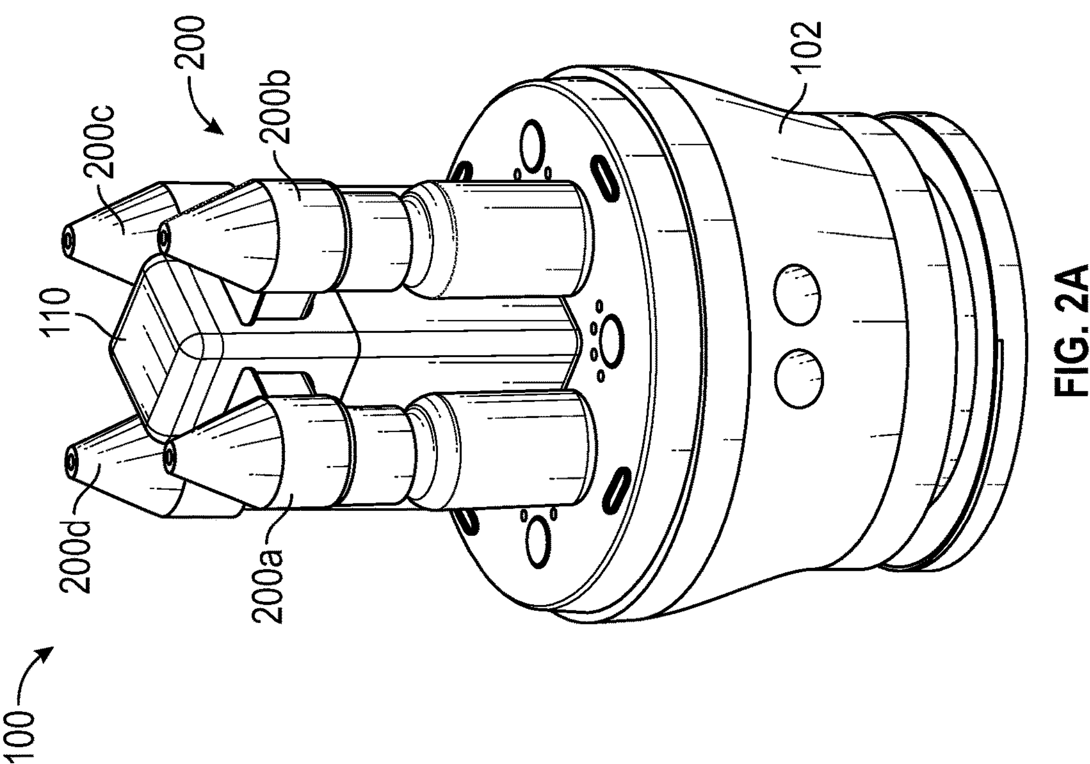
FIG. 2A depicts a perspective view of the diffuser of FIGS. 1A and 1B, without the cover.

Referring now to FIGS. 2A and 2B, diffuser 100 is shown with cover 104 removed. As shown in FIG. 2A, plurality of atomizers 200, e.g., atomizers 200*a*, 200*b*, 200*c*, 200*d*, may be removably coupled to stem portion 110 of diffuser 100. For example, atomizers 200 may be nebulizers. Stem portion 110 may have a square or rectangular cross-section having four planar faces, such that each atomizer 200*a*, 200*b*, 200*c*, 200*d* may be coupled to a respective face of stem portion 110. Although FIG. 2A illustrates diffuser 100 having four atomizers, as will be understood by a person having ordinary skill in the art, diffuser 100 may have less than four atomizers coupled to it at a time. In addition, stem portion 110 may have a different shaped cross-section having more than four planar faces, such that stem portion 110 may accommodate more than four atomizers.

Figure 3B:
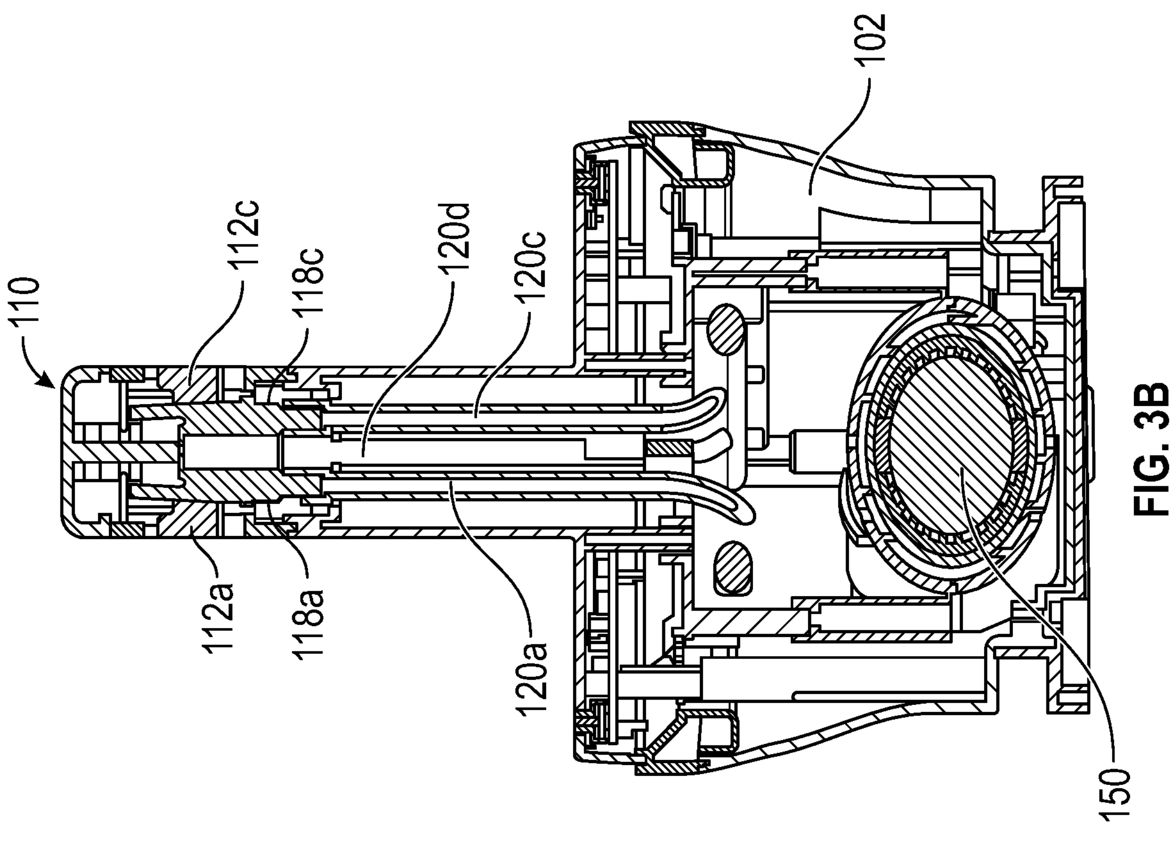
FIG. 3B depicts a cross-sectional view of the diffuser of FIG. 3A.
Figure 3A:
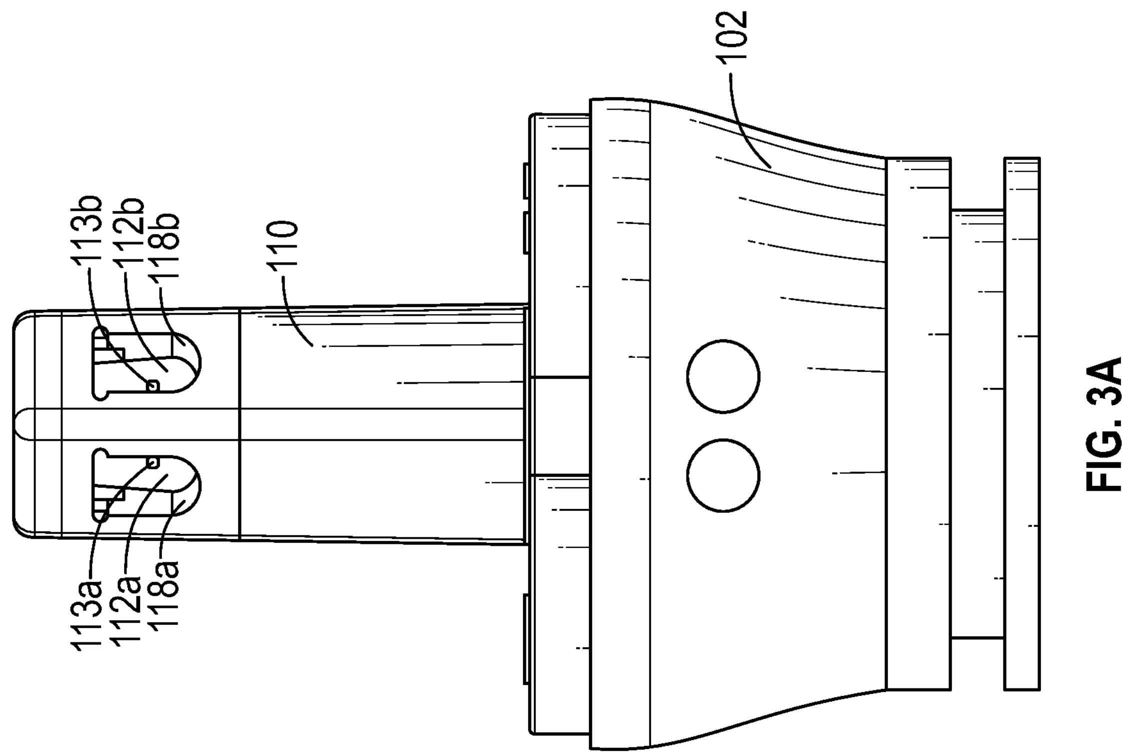
FIG. 3A depicts a front view the diffuser of FIGS. 2A and 2B, without the atomizers.
Figure 3C:
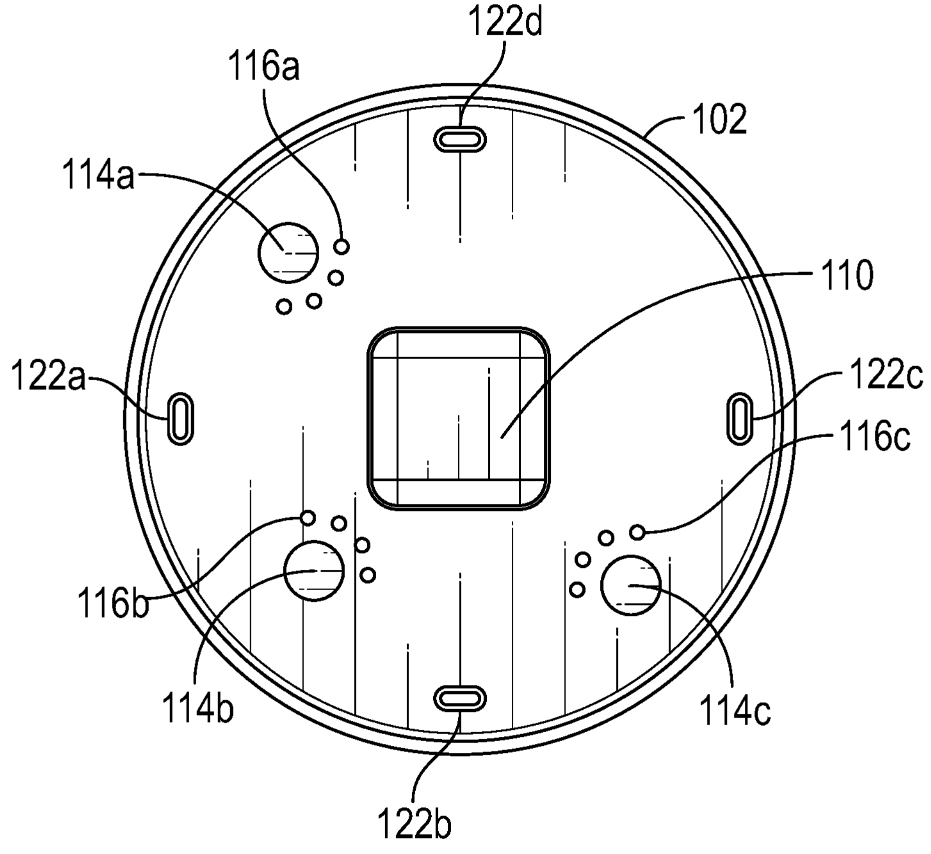
FIG. 3C depicts a top view of the diffuser of 3A.

Referring now to FIGS. 3A to 3C, diffuser 100 is shown with plurality of atomizers 200 removed. As shown in FIG. 3A, stem portion 110 may include a plurality of inlets, e.g., inlets 112*a*, 112*b*, for releasably engaging with a respective atomizer. Accordingly, stem portion 110 may have four inlets (inlets 112*c*, 112*d* not shown in FIG. 3A) for releasably engaging with four atomizers. Each inlet may have a shape corresponding with the shape of the connection portion of the atomizer, as described in further detail below. For example, as shown in FIGS. 3A and 3B, each inlet may have a rounded lower portion and a flat upper portion, and a groove, e.g., grooves 118*a*, 118*b*, 118*c* (groove 118*d* not shown in FIGS. 3A and 3B) for engaging with the lip of the connection portion of the atomizer. In addition, the outlet of each conduit, e.g., outlet 113*a*, 113*b*, 113*c*, 113*d*, is positioned within the respective inlet of stem portion 110, such that when the atomizer is coupled to stem portion 110 via the inlet, the passageway of the atomizer is in fluid communication with the respective conduit via the respective outlet, e.g., outlet 113*a*, 113*b*, 113*c*, 113*d*.

As shown in FIG. 3B, each inlet 112, 112*c* may be fluidicly coupled to pump 150 via a corresponding conduit, e.g., 118*a*, 118*c*. Each conduit may extend from pump 150 within base portion 102 through stem portion 110 to the respective inlet. Specifically, each conduit may be coupled to pump 150 via a valve, e.g., a solenoid valve (not shown), for selectively permitting flow from pump 150 through the respective conduit, as described in further detail below.

FIG. 3C is a top view of diffuser 100. As shown in FIG. 3C, base portion 102 may include a plurality of actuators 114*a*, 114*b*, 114*c*, 122*a*, 122*b*, 122*c*, 122*d* for executing a function of diffuser 100, and a plurality of indicators 116*a*, 116*b*, 116*c*, e.g., lights, associated with each of actuators 114*a*, 114*b*, 114*c*. For example, actuator 114*a* may be actuated by a user to select the length of a single diffusion by the plurality of atomizers, e.g., 5 seconds, 10 seconds, 15 seconds, or 20 seconds. Indicator 116*a* may include a number of lights corresponding with the number of options for a user to select from, e.g., four. Accordingly, based on the selection by the user by actuating indicator 116*a*, indicator 116*a* will indicate the length of diffusion that is currently selected.

In addition, actuator 114*b* may be actuated by a user to select the interval of diffusion by an atomizer, e.g., 5 seconds, 10 seconds, 30 seconds, or 60 seconds. Accordingly, actuation of actuator 114*b* will determine the length of time between diffusions by the plurality of atomizers. Indicator 116*b* may include a number of lights corresponding with the number of options for a user to select from, e.g., four. Accordingly, based on the selection by the user by actuating indicator 116*b*, indicator 116*b* will indicate the interval of diffusion that is currently selected.

Actuator 114*c* may be actuated by a user to select the duration of the diffusion program, e.g., 10 minutes, 20 minutes, 30 minutes, or 40 minutes. Indicator 116*c* may include a number of lights corresponding with the number of options for a user to select from, e.g., four. Accordingly, based on the selection by the user by actuating indicator 116*c*, indicator 116*c* will indicate the duration of the diffusion program that is currently selected. Thus, if the user selects 5 seconds length of diffusion via actuator 114*a*, 10 seconds interval of diffusion via actuator 114*b*, and 30 minutes duration of the diffusion program via actuator 114*c*, plurality of atomizers 200 of diffuser 100 will diffuse oil for 5 seconds at a time, every 10 seconds, for a total of 30 minutes. As will be understood by a person having ordinary skill in the art, the lengths of time described herein are merely illustrative and may vary.

Moreover, actuators 122*a*, 122*b*, 122*c*, 122*d* may be actuated to select one or more atomizers, e.g., atomizers 200*a*, 200*b*, 200*c*, 200*d*, respectively, for diffusion during the diffusion program. For example, the user may select any combination of atomizers 200*a*, 200*b*, 200*c*, 200*d* to be active during the diffusion program. Thus, if all four atomizers 200*a*, 200*b*, 200*c*, 200*d* are selected, then all four atomizers will diffuse their respective oils during the diffusion program, e.g., one at a time. If only atomizers 200*a* and 200*c* are selected, only atomizers 200*a*, 200*c* will diffuse their oils during the diffusion program, while atomizers 200*b* and 200*d* will not. Each atomizer may have a different oil stored therein, such that the user may select which combination of oils to diffuse during the diffusion program via actuators 122*a*, 122*b*, 122*c*, 122*d*. In addition, actuators 122*a*, 122*b*, 122*c*, 122*d* each may have an indicator, e.g., a light, associated therewith to indicate when the associated atomizer is selected.

Figure 4B:
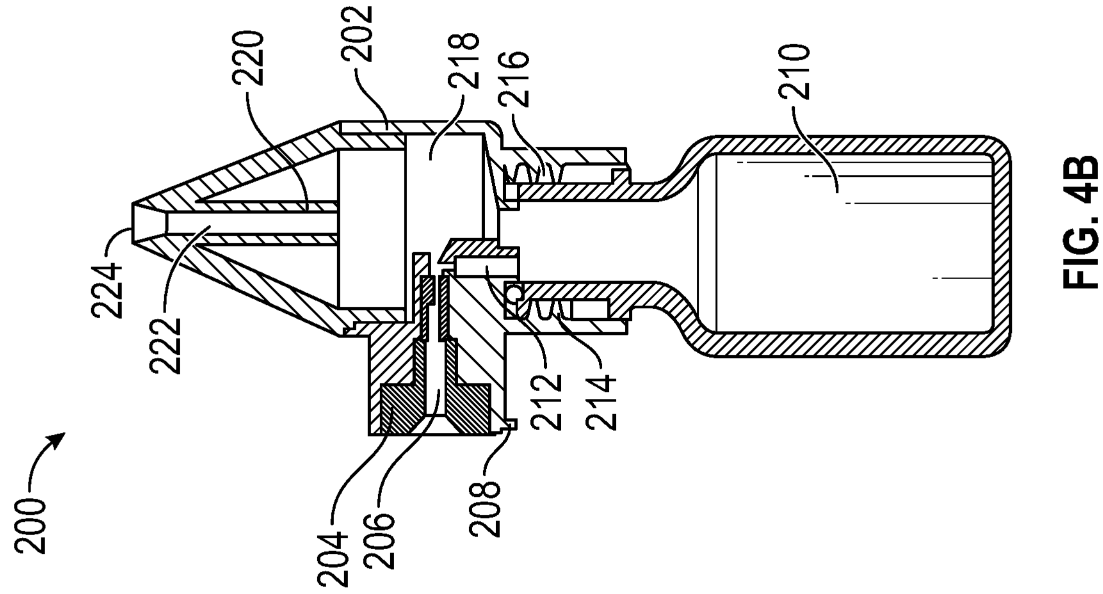
FIG. 4B depicts a cross-sectional view of the atomizer of FIG. 4A.
Figure 4A:
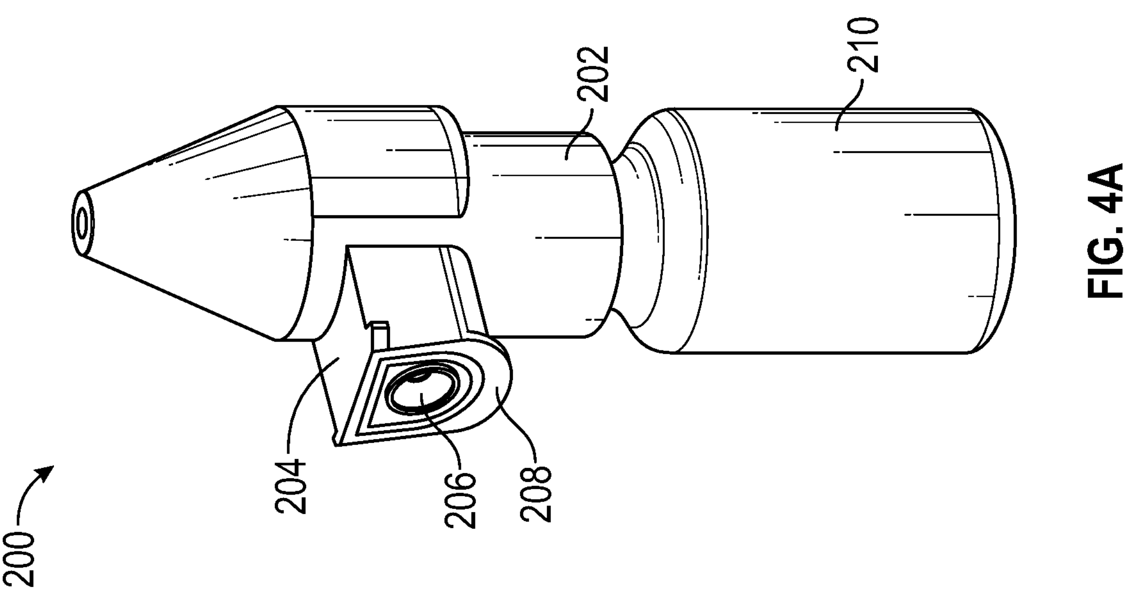
FIG. 4A depicts a perspective view of an atomizer, in accordance with one or more embodiments of the disclosure.

Referring now to FIGS. 4A and 4B, an exemplary atomizer is provided. Each of atomizers 200*a*, 200*b*, 200*c*, 200*d* may be constructed identically, and thus, are described herein collectively as atomizer 200. As shown in FIGS. 4A and 4B, atomizer 200 includes connection portion 202, which may be removably coupled to chamber 210. For example, chamber 210 may be disposable, such that when it is empty, it may be replaced with another full chamber. Alternatively, chamber 210 may be refillable, such that when it is empty, it may be decoupled from connection portion 202, refilled, and recoupled with connection portion 202. When coupled together, chamber 210 and connection portion 202 are in fluid communication. Chamber 210 may store one or more oils therein for diffusion via atomizer 200. As shown in FIG. 4B, chamber 210 may have threaded surface 216 which may engage with threaded surface 214 of connection portion 202, e.g., via a screw mechanism. Accordingly, chamber 210 may be removed from connection portion 202, for example, when chamber 210 needs to be refilled with the same or different oil.

In addition, connection portion 202 includes connection shaft 204 having passageway 206 extending therethrough, and sized and shaped to engage with the corresponding inlet of stem portion 110 of diffuser 100. Thus, the upper surface of connection shaft 204 may have a flat shape, and the bottom surface of connection shaft 204 may be rounded, to thereby correspond with the shape of the inlet of stem portion 110. Moreover, connection shaft 204 may have lip 208 sized and shaped to engage with the groove, e.g., groove 118*a*, of stem portion 110. For example, to engage atomizer 200 with the inlet, e.g., inlet 112*a*, of stem portion 110, connection shaft 204 may be inserted into the inlet, and then atomizer 200 may be pushed downward to engage lip 208 with the groove, e.g., groove 118*a*, to thereby secure atomizer 200 in place. When atomizer 200 is coupled to stem portion 110 via connection shaft 204 and the inlet, e.g., inlet 112*a*, passageway 206 is in fluid communication with the respective conduit of diffuser 100 and pump 150.

As shown in FIG. 4B, connection portion 202 includes suction chamber 217 which is in fluid communication with chamber 210 via passageway 212 when chamber 210 is coupled to connection portion 202, and in fluid communication with the respective conduit of diffuser 100 via passageway 206 when connection portion 202 is coupled to stem portion 110. For example, atomizer 200 includes a flexible tube (not shown) that extends from passageway 212 into and towards the bottom of chamber 210 for facilitating suction of the oil within chamber 210 into suction chamber 217 via the flexible tube and passageway 212. Accordingly, air and oil are mixed together in suction chamber 217. The mixture then moves to discharge chamber 218, where larger oil droplets are separated from the smaller oil droplets, such that the smaller oil droplets may be discharged through passageway 222 of connection portion 202, and the larger oil droplets flow back into chamber 210 via passageway 212. Passageway 222 includes inlet 220 and outlet 224. The upper portion of connection portion 202 may have a conical shape to facilitate diffusion. Accordingly, when atomizer 200 is selected, during the diffusion, the corresponding valve will permit flow from pump 150 through the respective conduit, and through passageway 206, which causes oil droplets to travel through passageway 212 into suction chamber 217. The mixed air and oil droplets will then enter discharge chamber 218, through inlet 220 of connection portion 202, and travel through passageway 222, and exit as a mist via outlet 224.

Figure 4D:
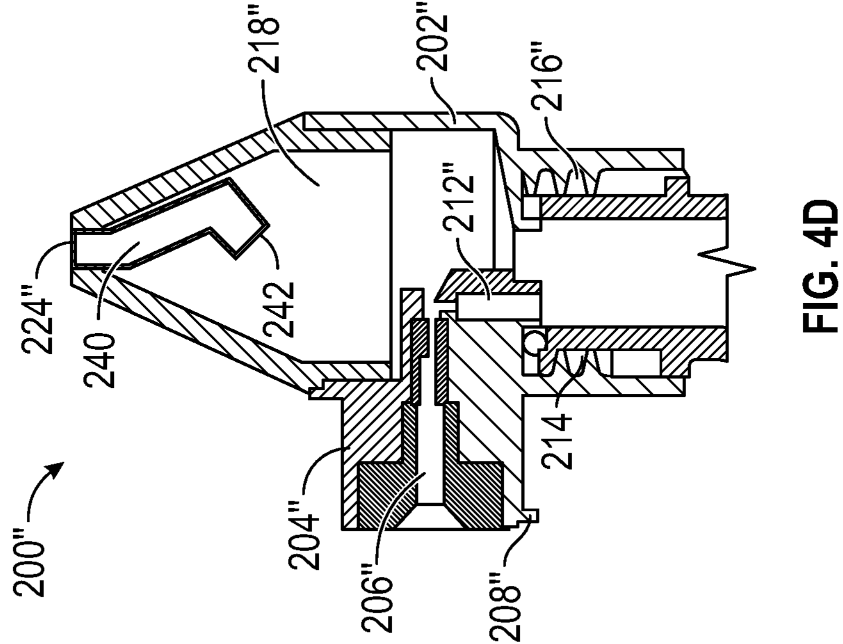
FIG. 4D depicts a cross-sectional view of an atomizer, in accordance with one or more embodiments of the disclosure.
Figure 4C:
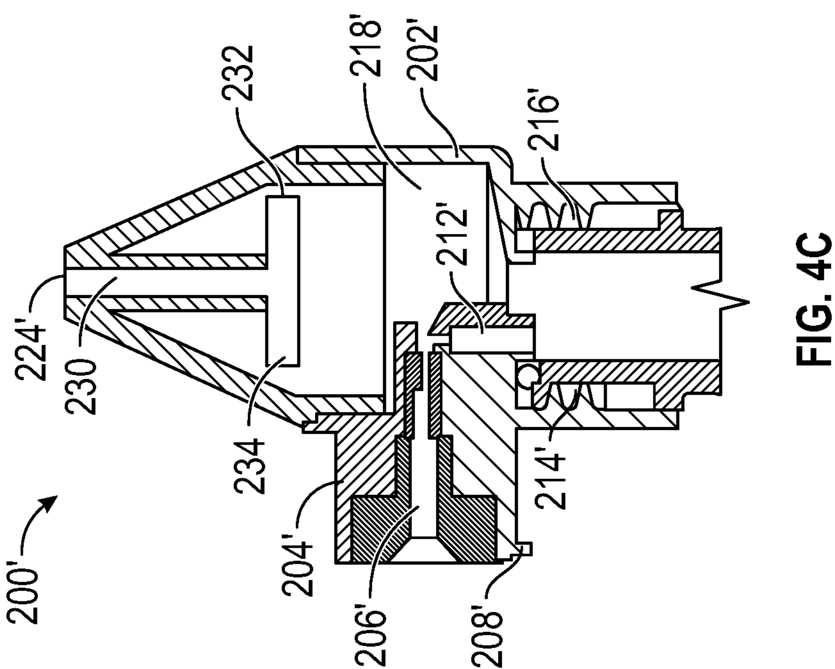
FIG. 4C depicts a cross-sectional view of an atomizer, in accordance with one or more embodiments of the disclosure.

Referring now to FIG. 4C, an alternative exemplary embodiment of the connection portion of the atomizer are provided. Atomizer 200' may be constructed similar to atomizer 200 of FIG. 4B, wherein like components are identified by like-primed reference numbers. For example, connection portion 202' corresponds with connection portion 202, passageway 206' corresponds with passageway 206, suction chamber 217' corresponds with suction chamber 217, discharge chamber 218' corresponds with discharge chamber 218, outlet 224' corresponds with outlet 224, etc. Atomizer 200' differs from atomizer 200 in that connection portion 202' has a tortuous passageway in fluid communication with outlet 224'. For example, as shown in FIG. 4C, connection portion 202' has T-shaped passageway 230 having first inlet 232 and second inlet 234 in fluid communication with discharge chamber 218'. T-shaped passageway 230 will prevent diffusion of larger oil droplets, e.g., oil droplets having a size exceeding a predetermined size, thereby reducing/preventing staining caused by the diffused oil vapor. The undiffused oil droplets will then collect at the bottom of discharge chamber 218' and suction chamber 217', and may return to chamber 210'.

Referring now to FIG. 4D, another alternative exemplary embodiment of the connection portion of the atomizer are provided. Atomizer 200" may be constructed similar to atomizer 200' of FIG. 4C, wherein like components are identified by like-double primed reference numbers. For example, connection portion 202" corresponds with connection portion 202', passageway 206" corresponds with passageway 206', suction chamber 217" corresponds with suction chamber 217', discharge chamber 218" corresponds with discharge chamber 218', outlet 224" corresponds with outlet 224', etc. Like atomizer 200', connection portion 202" of atomizer 200" has a tortuous passageway in fluid communication with outlet 224". However, as shown in FIG. 4D, connection portion 202" has zig zag-shaped passageway 240 having inlet 242 in fluid communication with discharge chamber 218". Zig zag-shaped passageway 240 will prevent diffusion of larger oil droplets, e.g., oil droplets having a size exceeding a predetermined size, thereby reducing/preventing staining caused by the diffused oil vapor. The undiffused oil droplets will then collect at the bottom of discharge chamber 218" and suction chamber 217", and may return to chamber 210". In addition, zig zag-shaped passageway 240 may include opening 241, e.g., a cut out, extending through zig zag-shaped passageway 240 in fluid communication with discharge chamber 218". For example, some oil particles may stick to the inner wall of zig zag-shaped passageway 240 over time, thereby obstructing flow through zig zag-shaped passageway 240, which may cause the oil droplets to bubble out of outlet 224" instead of a fine mist. Accordingly, oil, which may accumulate over time within zig zag-shaped passageway 240, may flow back into discharge chamber 218" via opening 241.

Figure 5A:
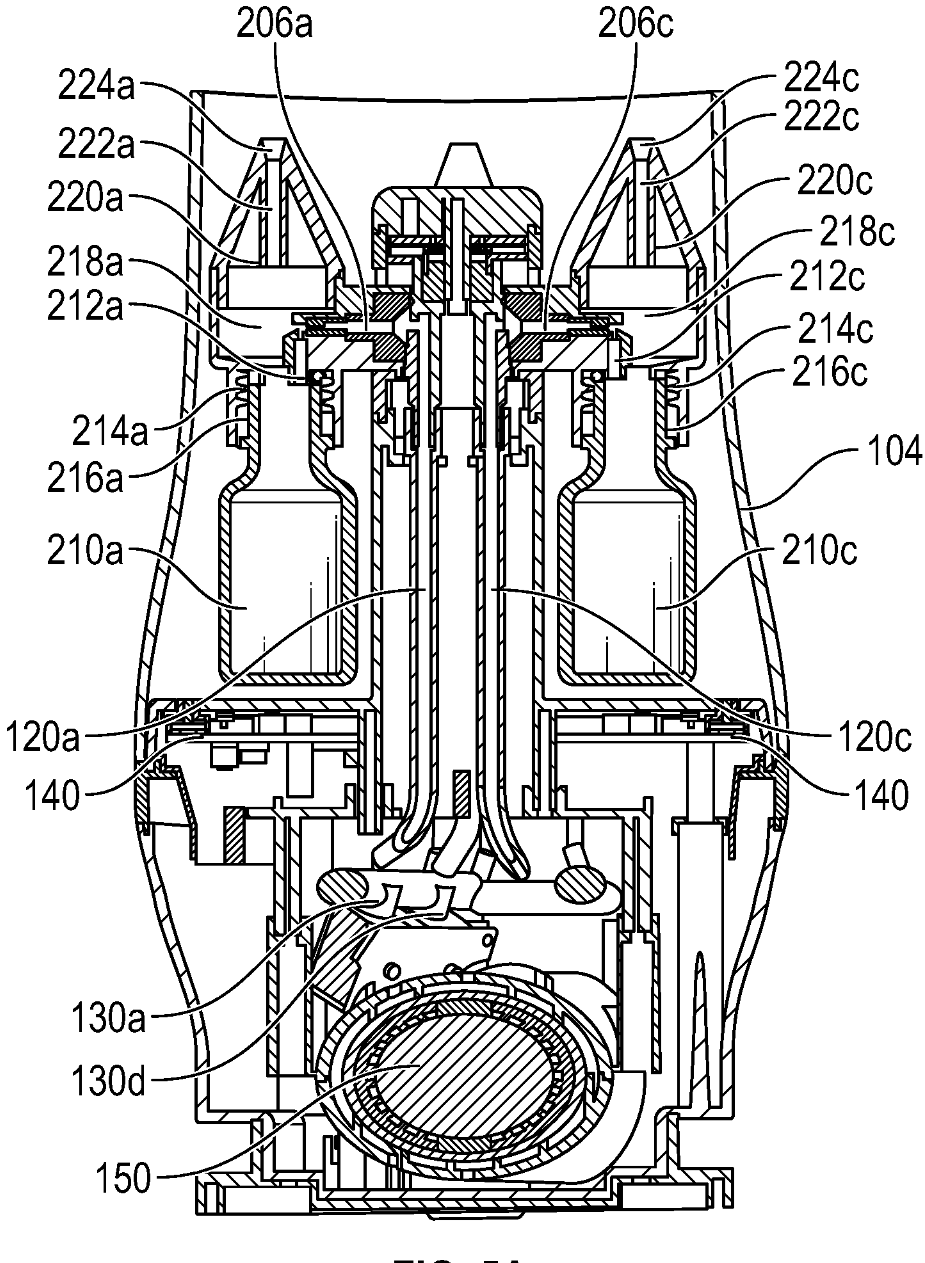
FIG. 5A depicts a cross-sectional view of the diffuser of FIGS. 1A and 1B.
Figure 5B:
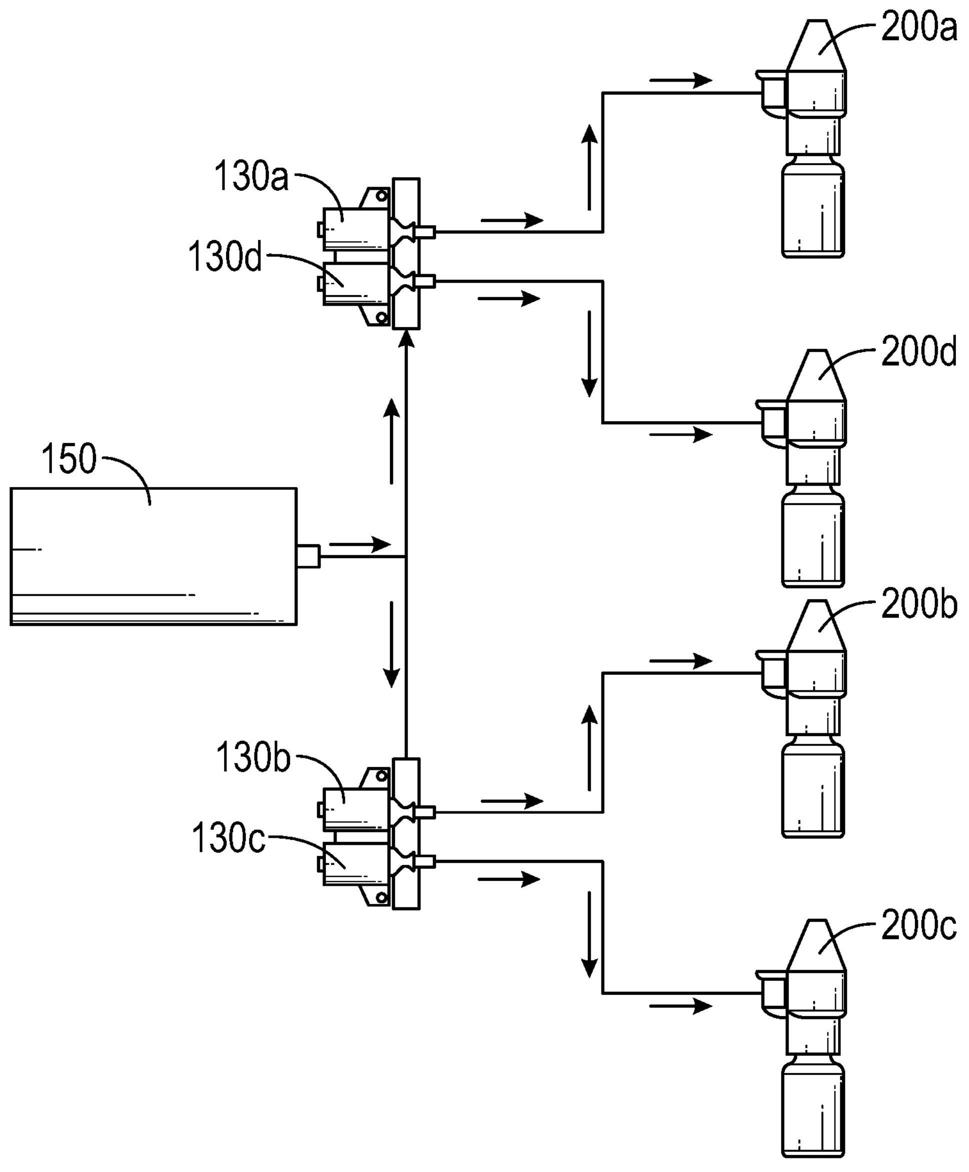
FIG. 5B is a schematic illustration of the air flow through the diffuser FIGS. 1A and 1B, in accordance with one or more embodiments of the disclosure.
Figure 6B:
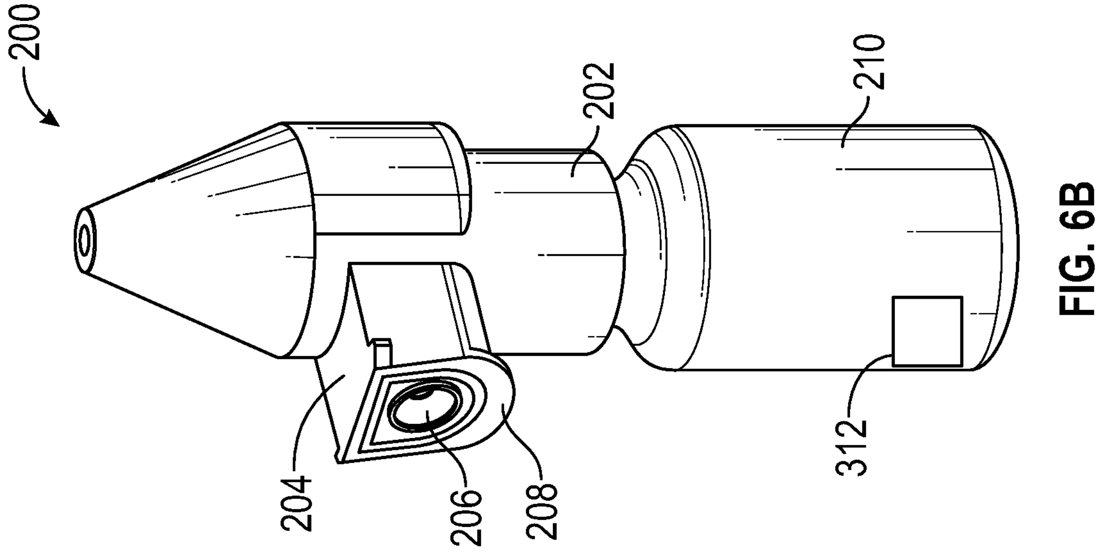
FIG. 6B depicts an atomizer for using with the diffuser of FIG. 6A, in accordance with one or more embodiments of the present disclosure.
Figure 6A:
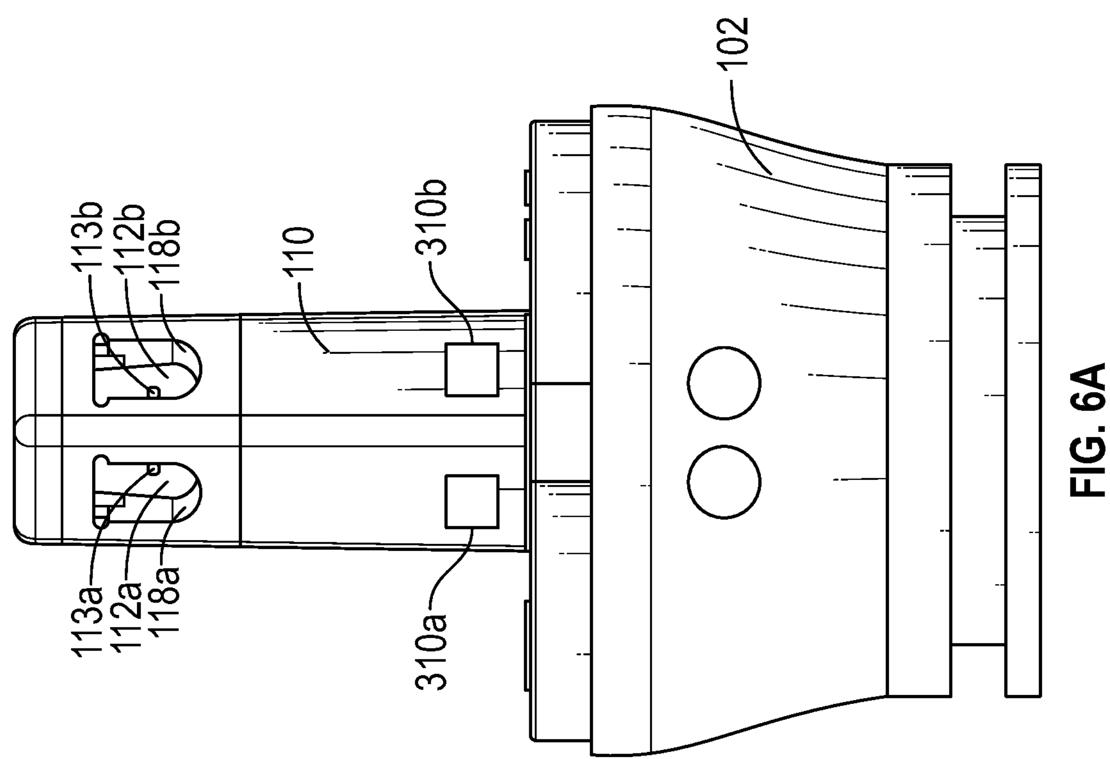
FIG. 6A depicts a front view of a diffuser have an oil balancer, in accordance with one or more embodiments of the present disclosure.
Figure 6C:
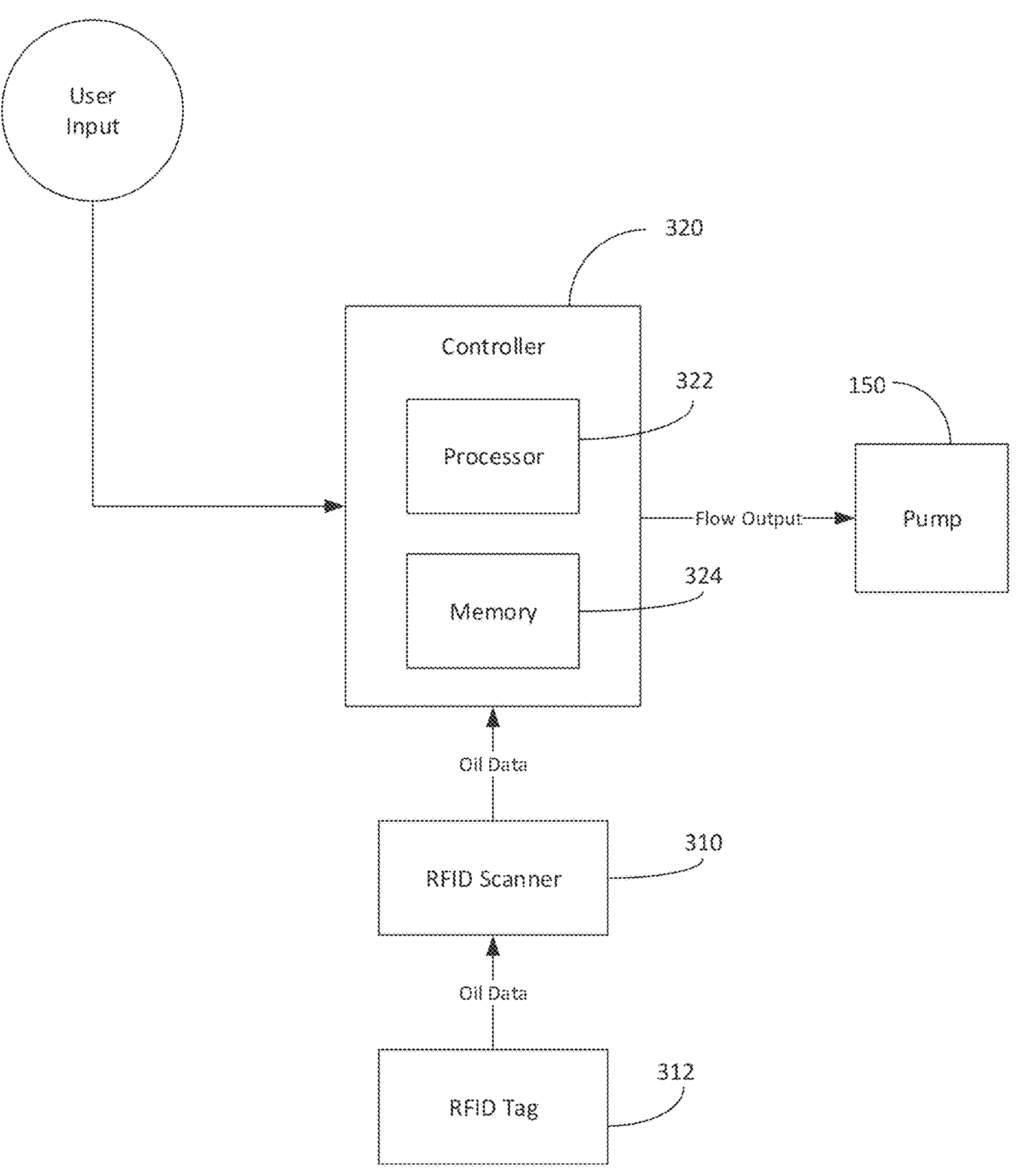
FIG. 6C is a flow chart of the oil balancing process, in accordance with one or more embodiments of the present disclosure.

Referring now to FIGS. 5A and 5B, the flow path of diffuser 100 is provided. As shown in FIG. 5B, air flows from pump 150 to four valves 130*a*, 130*b*, 130*c*, 130*d* (each valve associated with a respective conduit) which selectively permits flow through the associated conduit to the respective atomizer 200*a*, 200*b*, 200*c*, 200*d*. A pair of valves may share a common housing. For example, valves 130*a* and 130*d* may share a housing, and valves 130*b* and 130*c* may share another separate housing. As described above, each valve may be actuated to permit flow therethrough, responsive to selection of the atomizers via actuators 122*a*, 122*b*, 122*c*, 122*d*.

As shown in FIG. 5A, diffusor 100 further may include one or more circuit boards 140 for electrically coupling the actuators with pump 150 and valves 130*a*, 130*b*, 130*c*, 130*d*. Thus, upon selection by the user of which atomizers to activate, length of diffusion, interval of diffusion, and duration of diffusion program via the associated actuators, the valves associated with the selected atomizers, e.g., valves 130*a*, 130*b*, 130*c*, 130*d*, will permit flow therethrough from pump 150. Air will flow through the corresponding conduit, e.g., conduit 120*a*, 120*b*, 120*c*, 120*d*, and into the respective passageway of the selected atomizer, e.g., passageway 206*a*,

206*b*, 206*c*, 206*d*, thereby causing the oil in the chamber of the selected atomizers to travel through the respective passageway, e.g., passageways 212*a*, 212*b*, 212*c*, 212*d*, and into the respective suction chamber, e.g., suction chambers 217*a*, 217*b*, 217*c*, 217*d*. The air/oil mix will then travel to the respective discharge chamber, e.g., discharge chambers 218*a*, 218*b*, 218*c*, 218*d*, and through the respective passageway, e.g., passageways 222*a*, 222*b*, 222*c*, 222*d*, and exit the respective outlet, e.g., outlets 224*a*, 224*b*, 224*c*, 224*d*, in a mist form.

Diffusor 100 may also include oil balancer 300. In embodiments, pump 150 may control simultaneous diffusion of multiple oils, where oil balancer 300 is effective to control the rate of diffusion of the respective oils during simultaneous diffusion. Oil balancer 300 includes radio frequency identification (RFID) reader, e.g., RFID readers 310*a*, 310*b*, 310*c*, 310*d* disposed about stem portion 110. In embodiments, stem portion 110 is rectangular, such that each RFID reader 310*a*, 310*b*, 310*c*, 310*d* is positioned on a side of stem portion 110. In other embodiments, one or more RFID readers 310*a*, 310*b*, 310*c*, 310*d* may be positioned anywhere on diffuser 100.

Each RFID reader 310*a*, 310*b*, 310*c*, 310*d* corresponds with a respective RFID tag, e.g., RFID tags 312*a*, 312*b*, 312*c*, 312*d*. Each RFID tag 312*a*, 312*b*, 312*c*, 312*d* is positioned on respective atomizers 200*a*, 200*b*, 200*c*, 200*d* and store information pertaining to the oils contained within each atomizer. This information includes, but is not limited to, the viscosity and potency of the oils. RFID readers 310*a*, 310*b*, 310*c*, 310*d* may read the data from the respective RFID tags 312*a*, 312*b*, 312*c*, 312*d* and transmits the data to controller 320. In some embodiments, one or more RFID tags 312*a*, 312*b*, 312*c*, 312*d* may be positioned anywhere on the atomizer, canister, or other similar component of diffuser 100.

Controller 320 has processor 322 and memory 324 that together form a computing device. Controller 320 may be configured to execute the steps, processes, and functions disclosed herein, and controls components of diffuser 100 based on one or more inputs. For example, a user may select up to four oils for simultaneous diffusion. That is, the user may select two, three, or four oils to diffuse simultaneously, or alternatively, the user may also select a single oil, in which case oil balancer 300 would remain inactive. When multiple oils are selected, controller 320 determines an optimized flow rate for each selected oil and controls airflow from pump 150 to each atomizer 200*a*, 200*b*, 200*c*, 200*d* accordingly to achieve balanced diffusion.

To determine the ideal flow rate for the selected oils, controller 320 reads and process the data collected from RFID tags 312*a*, 312*b*, 312*c*, 312*d* to balance the diffusion of each of the selected oils. For example, some oils may have a more potent scent that will overpower the scent of other oils during simultaneous diffusion. From the RFID tag information, the controller 320 can identify these potent oils and adjust the flow rate accordingly, i.e., lowering the flow rate, so that the scent of one oil does not overpower that of any of the other oils.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, one skilled in the art will recognize such feature, structure, or characteristic in connection with other embodiments whether or not explicitly described.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described example embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A diffuser comprising:

a pump;

a plurality of atomizers, each atomizer of the plurality of atomizers coupled to the pump via a respective conduit; and a valve associated with each of the conduits and configured to selectively permit flow from the pump to the respective atomizer; and an oil balancer comprising a controller, wherein the oil balancer is configured to receive one or more oil properties from a RFID tag corresponding with each atomizer of the plurality of atomizers and, based on the one or more oil properties, control the atomizers to dictate a rate of flow from each atomizer to balance diffusion of two or more scents from the plurality of atomizers.

2. The diffuser of claim 1, wherein the plurality of atomizers comprises four or more atomizers.

3. The diffuser of claim 1, wherein the plurality of atomizers is configured to hold one or more oils.

4. The diffuser of claim 1, wherein each atomizer of the plurality of atomizers comprises a connection portion configured to be coupled to the respective conduit, the connection portion configured to be removably coupled to a chamber portion configured to hold oil.

5. The diffuser of claim 1, further comprising:

a base portion configured to house the pump; and a stem portion extending from the base portion, wherein the conduits are configured to extend from the pump through the stem portion.

6. The diffuser of claim 5, wherein each atomizer of the plurality of atomizers is configured to be removably coupled to the respective conduit via the stem portion.

7. The diffuser of claim 5, further comprising a cover configured to be removably coupled to the base, the cover surrounding the stem portion when coupled to the base.

8. The diffuser of claim 1, further comprising a control module operatively coupled to the pump and the valve, the control module configured to activate the pump and selectively activate the valve to permit flow from the pump to the respective atomizer responsive to actuation.

9. The diffuser of claim 8, wherein the control module is configured to permit a user to select at least one of length of diffusion, interval of diffusion, or length of operation of diffuser.

10. An atomizer comprising:

a connection portion comprising an inlet configured to be coupled to a pump, an outlet, and a discharge chamber in fluid communication with the inlet and the outlet, the connection portion configured to be removably and fluidically coupled to a chamber portion configured to hold oil, wherein the outlet comprises a tortuous pathway configured to prevent diffusion of droplets of the oil exceeding a predetermined size upon actuation of the pump, and wherein diffusion of the oil from the atomizer is controlled by a controller, with the diffusion being based on one or more oil properties received by the controller from a RFID tag corresponding with the atomizer, wherein the controller is configured to dictate a rate of flow from each atomizer to balance diffusion of two or more scents from the plurality of atomizers.

11. The atomizer of claim 10, wherein the tortuous pathway comprises a T-shape.

12. The atomizer of claim 10, wherein the tortuous pathway comprises a zig zag shape.

13. The atomizer of claim 10, wherein the inlet of the connection portion comprises a lip configured to engage with a groove of a housing of the pump.

14. The atomizer of claim 10, wherein undiffused droplets of oil within the connection portion are configured to return to the chamber portion.

15. A diffuser comprising:

a pump;

a plurality of atomizers, each atomizer of the plurality of atomizers coupled to the pump via a respective conduit;

a valve associated with each of the conduits and configured to selectively permit flow from the pump to the respective atomizer; and an oil balancer comprising:

a plurality of RFID readers, a plurality of RFID tags, and a controller;

wherein the oil balancer is configured to receive one or more oil properties from a RFID tag corresponding with each atomizer of the plurality of atomizers and, based on the one or more oil properties, control the atomizers to dictate a rate of flow from each atomizer to balance diffusion of two or more scents from the plurality of atomizers.

16. The diffuser of claim 15, further comprising:

a base portion configured to house the pump; and a stem portion extending from the base portion, wherein the conduits are configured to extend from the pump through the stem portion.

17. The diffuser of claim 16, wherein each RFID reader of the plurality of RFID readers is located on the stem portion of the diffuser.

18. The diffuser of claim 15, wherein each atomizer of the plurality of atomizers comprises an oil.

19. The diffuser of claim 18, wherein each RFID tag of the plurality of RFID tags is located on a corresponding atomizer of the plurality of atomizers, and wherein the RFID tag corresponds with the oil of the atomizer on which the RFID tag is located.

20. The diffuser of claim 19, wherein each RFID reader of the plurality of RFID readers is configured to read a corresponding RFID tag of the plurality of RFID tags, such that when a user selects one or more of the plurality of atomizers for diffusion, each RFID reader reads data from the corresponding RFID tag and transmits the data to the controller, wherein the controller uses the data to determine the optimal flow rate for each atomizer when more than one atomizer is selected, so as to enable balanced simultaneous diffusion.

* * * * *